United States Patent [19]

Miller

[11] Patent Number: 4,608,450
[45] Date of Patent: * Aug. 26, 1986

[54] TWO-STAGE MULTIFORMING OF OLEFINS TO TETRAMERS

[75] Inventor: Stephen J. Miller, San Francisco, Calif.

[73] Assignee: Chevron Research Company, San Francisco, Calif.

[*] Notice: The portion of the term of this patent subsequent to Nov. 8, 2000 has been disclaimed.

[21] Appl. No.: 639,978

[22] Filed: Aug. 10, 1984

[51] Int. Cl.$^4$ ............................................. C07C 2/02
[52] U.S. Cl. ................................. 585/517; 585/533
[58] Field of Search ........................................ 585/517

[56] References Cited

U.S. PATENT DOCUMENTS 4,414,423 11/1983 Miller .................................. 585/517

Primary Examiner—Curtis R. Davis
Attorney, Agent, or Firm—S. R. LaPaglia; W. K. Turner; V. J. Cavalieri

[57] ABSTRACT

A two-stage process for preparing a $C_3$ or $C_4$ olefin tetramer using nickel-containing HZSM-5 zeolite catalyst is disclosed. The tetramer so formed may be used to make high quality middle distillates such as jet fuel or as a petrochemical feed for making detergents.

10 Claims, 3 Drawing Figures

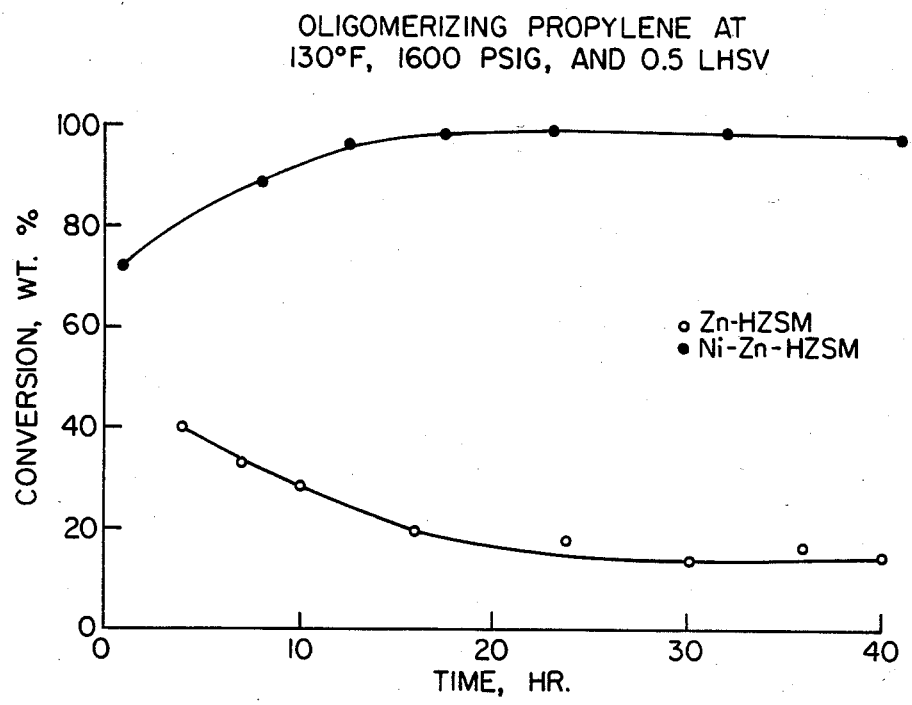
FIG._1.
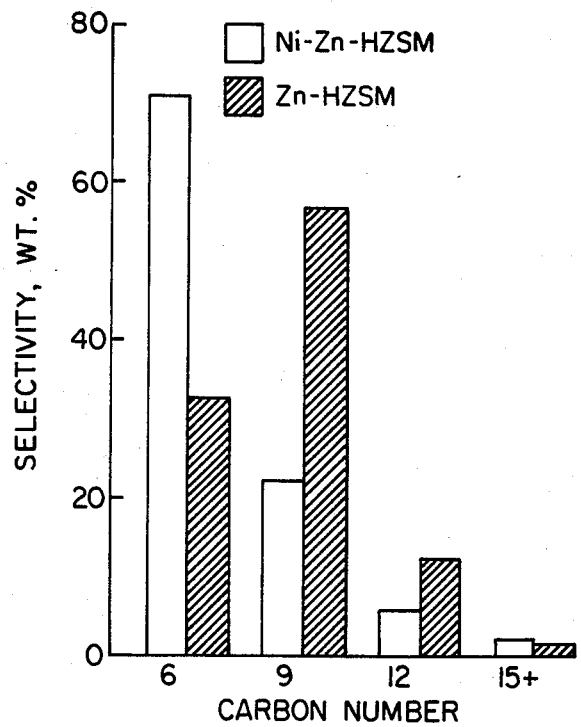
FIG._2.

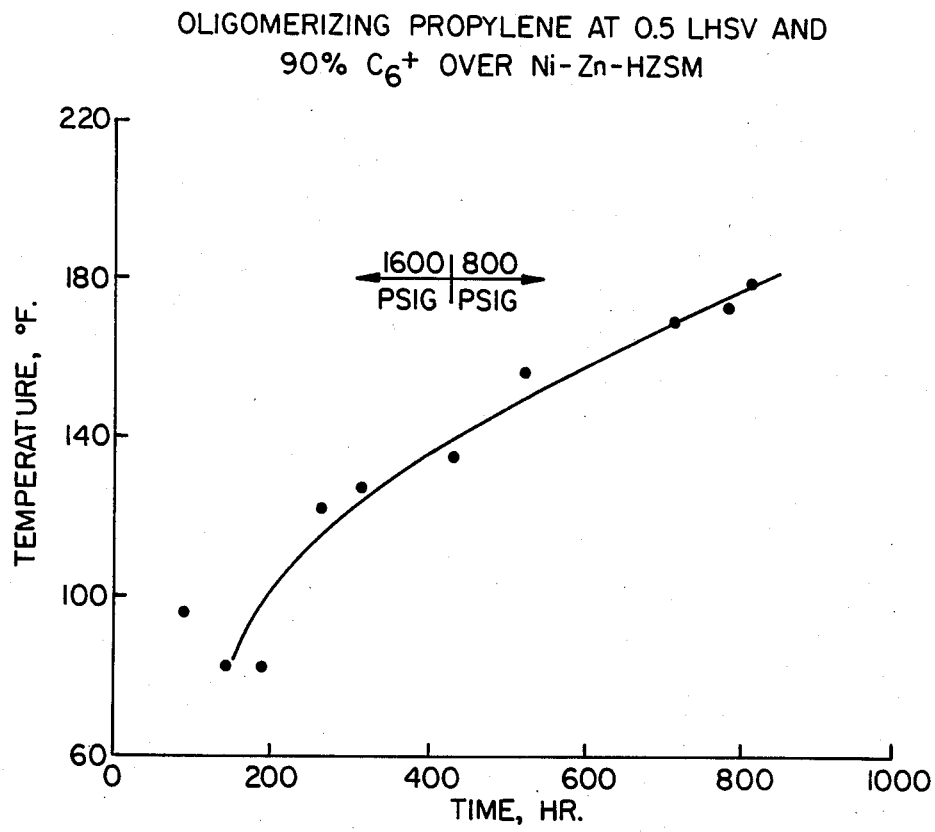
FIG._3.

TWO-STAGE MULTIFORMING OF OLEFINS TO TETRAMERS

TECHNICAL BACKGROUND

The present invention relates to a method for making a $C_3$ or $C_4$ olefin tetramer. More specifically, the present invention relates to a two-stage multiforming of $C_3$ or $C_4$ olefins or mixtures thereof to tetramer over a nickel-containing HZSM-5 zeolite catalyst. $C_3$ and $C_4$ tetramers and especially propylene tetramer are very useful petrochemical feeds for making detergents such as alkylbenzene sulfonates, and for making high quality middle distillates such as jet fuel.

Olefin dimerization, oligomerization, and polymerization processes are well known in the art. However, current processes have limited selectivity to tetramer and/or require large recycle of light polymer ($C_6$–$C_9$), thus limiting throughput.

It has now been found that the described disadvantages for preparing $C_3$ and $C_4$ olefin tetramers can be eliminated or at least greatly reduced by a process which involves a high once-through conversion of $C_3$ and $C_4$ olefins or mixtures thereof to the corresponding tetramer by contacting the olefins in the liquid form with Ni-HZSM-5 in a two-stage process.

TECHNICAL DISCLOSURE

In accordance with the present invention, there has been discovered a process for preparing a $C_3$ and $C_4$ olefinic tetramer comprising:

(a) contacting in a first stage a $C_3$ or $C_4$ olefin stream or mixture thereof in the liquid state with an Ni-HZSM-5 catalyst at a temperature of from about 80° to 200° F. and a pressure of about 400 to 1600 psig to produce a first effluent containing at least 70% by weight dimer of said $C_3$ or $C_4$ olefin; and (b) contacting in a second stage the first effluent in the liquid state with a second Ni-HZSM-5 catalyst at a temperature of from about 250° to 450° F. and a pressure of 200 to 800 psig to produce a second effluent containing at least 60% tetramer of said $C_3$ or $C_4$ olefin or mixture thereof.

The $C_3$ or $C_4$ feed alkenes can be prepared from many sources by standard methods. Almost all commercially produced $C_3$ and $C_4$ alkenes are obtained as by-products from two principal process: catalytic or thermal cracking, refinery processes which upgrade high boiling petroleum fractions to gasoline; and steam cracking which produces light olefins for chemical feedstocks by pyrolysis of saturated hydrocarbons derived from natural gas or crude oil.

The $C_3$ and $C_4$ olefins from the above processes may initially be available as a $C_3$ and $C_4$ olefin mixture which may be used directly or which may be fractionated to a $C_3$ cut and a $C_4$ cut; it may also be available in the form of previously separated $C_3$ and $C_4$ fractions, as obtained, for example, by distillation of the effluent from a catalytic cracking unit.

As described in U.S. Pat. No. 4,268,701 which reference is incorporated herein by reference, when the catalytic cracking product appears as separate $C_3$ and $C_4$ cuts, their composition is, for example, by weight:

| $C_3$ cut: | propane | 15 to 50% |
|---|---|---|
| | propylene | 50 to 85% |
| $C_4$ cut: | n-butane | 5 to 20% |
| | isobutane | 20 to 50% |
| | isobutene | 10 to 25% |
| | 1-butene | 5 to 15% |
| | 2-butene | 10 to 40% |

It has been found that the present process provides selective conversion of the $C_3$ or $C_4$ olefin feed or mixture of $C_3$ and $C_4$ olefin feed to tetramer products. The first stage of the process effects the conversion of the $C_3$ or $C_4$ olefin feed to dimers, and the second stage of the process effects the conversion of dimer from the first stage to tetramer products with high selectivity. The product of the present two-stage process thus contains primarily olefin tetramer and little or no light cracked products, paraffins, etc.

The reaction conditions in the first reaction zone are such as to cause the $C_3$ or $C_4$ olefin or mixture thereof in the liquid state to oligomerize about 90% to 99% of the olefin to form an effluent which contains at least about 70% by weight dimer and preferably from about 75% to 80% by weight dimer. The first reaction zone can be operated at temperatures from about 80° F. to 200° F., pressures from about 400 psig to 1600 psig, and hourly space velocities of from about 0.5 to 2.

The feed to the second step of the process contains the normally liquid dimer olefins produced by the first step. The second step is operated so that the dimers produced in this second step are liquids under the conditions in that reaction zone. The second reaction zone can be operated at temperatures of from about 250° F. to 450° F., pressures from about 200 psig to 800 psig, and hourly space velocities from about 0.5 to 4. The once-through conversion to tetramer, based on starting $C_3$ or $C_4$ olefin, can be 60% or more.

The tetramers which are the products of the process of this invention are highly useful for both fuels and chemicals. As a fuel, the tetramers serve as extremely high quality midbarrel fuels, such as jet fuel. These $C_3$ and $C_4$ tetramers can also undergo chemical reactions to produce surfactants which in turn can be used as additives to improve the operating characteristics of the compositions to which they are added (e.g., lubricating oils) or can be used as primary surfactants in highly important activities such as enhanced oil recovery or as detergents. Among the most used surfactants prepared from the tetramers are alkyl sulfonates and alkyl benzene sulfonates.

A significant feature of the present process is the liquid phase contacting of the olefin feed in both the first and second stages and the nickel-HZSM-5 crystalline molecular sieve. There will be appreciated that the pressures and temperatures employed must be sufficient to maintain the system in the liquid phase. As is known to those in the art, the pressure will be a function of the feed olefin and the temperature.

The two-stage mutiforming process described herein may be carried out as a batch type, semi-continuous or continuous operation utilizing fixed or moving bed catalyst system.

BRIEF DESCRIPTION OF THE DRAWINGS

FIG. 1 is a graph showing the conversion of propylene to higher molecular weight products as a function of time at 130° F., 1600 psig, and 0.5 LHSV for two different catalysts.

FIG. 2 is a graph showing the carbon number selectivity for oligomerizing propylene at 130° F., 1600 psig, and 0.5 LHSV for two different catalysts.

FIG. 3 is a graph showing a plot of temperature for 90% conversion of propylene to $C_6+$ over Ni-Zn-HZSM-5 catalyst versus time under the conditions shown.

DESCRIPTION OF SPECIFIC EMBODIMENTS

The nickel-containing HZSM-5 zeolite is a silicaceous crystalline molecular sieve of intermediate pore size. By "intermediate pore size", as used herein, is meant an effective pore aperture in the range of about 5 to 6.5 Angstroms when the molecular sieve is in the H-form. Molecular sieves having pore apertures in this range tend to have unique molecular sieving characteristics. Unlike small pore zeolites such as erionite and chabazite, they will allow hydrocarbons having some branching into the molecular sieve void spaces. Unlike larger pore zeolites such as the faujasites and mordenites, they can differentiate between n-alkanes and slightly branched alkanes on the one hand and larger branched alkanes having, for example, quaternary carbon atoms.

The effective pore size of the molecular sieves can be measured using standard adsorption techniques and hydrocarbonaceous compounds of known minimum kinetic diameters. See Breck, *Zeolite Molecular Sieves*, 1974 (especially Chapter 8) and Anderson et al, J. Catalysis 58, 114 (1979), both of which are incorporated by reference.

Intermediate pore size molecular sieves in the H-form will typically admit molecules having kinetic diameters of 5.0 to 6.5 Angstroms with little hindrance. Examples of such compounds (and their kinetic diameters in Angstroms) are: n-hexane (4.3), 3-methylpentane (5.5), benzene (5.85), and toluene (5.8). Compound having kinetic diameters of about 6 to 6.5 Angstroms can be admitted into the pores, depending on the particular sieve, but do not penetrate as quickly and in some cases are effectively excluded. Compounds having kinetic diameters in the range of 6 to 6.5 Angstroms include: cyclohexane (6.0), 2,3-dimethylbutane (6.1), m-xylene (6.1), and 1,2,3,4-tetramethylbenzene (6.4). Generally, compounds having kinetic diameters of greater than about 6.5 Angstroms do not penetrate the pore apertures and thus are not absorbed into the interior of the molecular sieve lattice. Examples of such larger compounds include: o-xylene (6,8), hexamethylbenzene (7.1), 1,3,5-trimethylbenzene (7.5), and tributylamine (8.1).

In performing adsorption measurements to determine pore size, standard techniques are used. It is convenient to consider a particular molecule as excluded if it does not reach at least 95% of its equilibrium adsorption value on the zeolite in less than about 10 minutes (p/po=0.5; 25° C.).

Nickel-containing HZSM-5 is described in U.S. Pat. Nos. 3,702,886 and 3,770,614.

When synthesized in the alkali metal form, the ZSM-5 zeolite may be conveniently converted to the hydrogen form by well-known ion exchange reactions, for example, by intermediate formation of the ammonium form as a result of ammonium ion exchange and calcination of the ammonium form to yield the hydrogen form, as disclosed in U.S. Pat. No. 4,211,640, or by treatment with an acid such as hydrochloric acid as disclosed in U.S. Pat. No. 3,702,886.

Nickel is incorporated into the silicaceous crystalline molecular sieve according to techniques well known in the art such as impregnation and cation exchange. For example, typical ion exchange techniques would be to contact the particular sieve in the hydrogen form with an aqueous solution of a nickel salt. Although a wide variety of salts can be employed, particular preference is given to chlorides, nitrates and sulfates. The amount of nickel in the zeolites range from 0.5% to 10% by weight and preferably from 1% to 5% by weight.

Representative ion exchange techniques are disclosed in a wide variety of patents including U.S. Pat. Nos. 3,140,249; 3,140,251; 3,960,978; and 3,140,253.

Following contact with the salt solution, the zeolites are preferably washed with water and dried at a temperature ranging from 150° F. to about 500° F. and thereafter heated in air at temperatures ranging from about 500° F. for periods of time ranging from 1 to 48 hours or more.

The nickel-containing HZSM-5 zeolite catalyst can be made substantially more stable for oligomerization by including from about 0.2% to 3% by weight and preferably 0.5% to 2% by weight of the Group IIB metals, zinc or cadmium and preferably zinc. A primary characteristic of these substituents is that they are weak bases, and are not easily reduced. These metals can be incorporated into the catalysts using standard impregnation, ion exchange, etc., techniques. Strongly basic metals such as the alkali metals are unsatisfactory as they poison substantially all of the polymerization sites on the zeolite. For this reason, the alkali metal content of the zeolite is less than 1%, preferably less than 0.1%, and most preferably less than 0.01%. The feed should be low in water, i.e., less than 100 ppm, more preferably less than 10 ppm, in sulfur, i.e., less than 100 ppm and preferably less than 10 ppm, in diolefins, i.e., less than 0.5%, preferably less than 0.05% and most preferably less than 0.01%, and especially in nitrogen, i.e., less than 5 ppm, preferably less than 1 ppm and most preferably less than 0.2 ppm.

The polymerization process of the present invention is surprisingly more efficient with small crystallite sieve particles than with larger crystalline particles. Preferably, the molecular sieve crystals or crystallites are less than about 10 microns, more preferably less than about 1 micron, and most preferably less than about 0.1 micron in the largest dimension. Methods for making molecular sieve crystals in different physical size ranges are known to the art.

The molecular sieves can be composited with inorganic matrix materials, or they can be used with an organic binder. It is preferred to use an inorganic matrix since the molecular sieves, because of their large internal pore volumes, tend to be fragile, and to be subject to physical collapse and attrition during normal loading and unloading of the reaction zones as well as during the oligomerization processes. Where an inorganic matrix is used, it is preferred that the matrix be substantially free of hydrocarbon conversion activity.

Once the effluent from the oligomerization reaction zone is recovered, a number of further processing steps can be performed.

If it is desired to use the long chain compounds directly as fuels, the $C_3$ or $C_4$ olefin tetramers can be hydrogenated.

All or part of the effluent of the second zone can be contacted with the molecular sieve catalyst in further reaction zones to further react the olefin tetramers with themselves to form still longer chain materials. Of course, the longer the carbon chain, the more susceptible the compound is to being cracked. Therefore, where successive oligomerization zones are used, the oligomerization zones must be operated under conditions which will not cause the oligomers to crack or engage in hydrogen transfer reactions. The most convenient, and preferred, method of operation where multiple reaction zones are used, is to operate each zone under reaction conditions less severe than the preceding oligomerization zone. Operating with oligomerization zones in series with decreasing severity makes process control of the exothermic oligomerization reactions much easier.

One particularly desirable method of operation is to separate unreated $C_3$ or $C_4$ olefin present in the first effluent and then to recycle the unreacted olefin back into the feed. In the same way, unreacted $C_3$ or $C_4$ olefin dimer can be separated from the second effluent and then recycled back into the feed for the second-stage reaction.

The following examples illustrate the practice of the present method.

EXAMPLES

Example 1

HZSM-5 zeolite of 80 $SiO_2/Al_2O_3$ mole ratio was mixed with peptized Catapal alumina at a 50/50 sieve/alumina weight ratio, extruded through a 1/16" die, dried overnight at 300° F. under $N_2$, then calcined in air for eight hours at 850° F. The catalyst was exchange five times with a 1% aqueous ammonium acetate solution, then washed with water to give a final Na level of 100 ppm.

Example 2

The catalyst of Example 1 was impregnated by the pore-fill method with 1% Zn using an aqueous solution of zinc nitrate, then dried and calcined as in Example 1.

Example 3

The catalyst of Example 1 was exchanged with a 1% aqueous nickel acetate solution at 180° F. for five hours, washed with water, then dried and calcined as in Example 1. The Ni content of the calcined catalyst was 3 wt %.

Example 4

The catalyst of Example 3 was impregnated with 1% Zn, dried, and calcined as in Example 1.

Example 5

The catalyst of Example 2 (Zn-HZSM-5) was tested for conversion of propylene to higher molecular weight products at 130° F., 1600 psig, and 0.5 LHSV. At 40 hours on stream, conversion to $C_6+$ was less then 20 wt %.

The propylene dimer distribution is given in Table 1.

TABLE 1

| $C_6$ Olefin Composition From Propylene Oligomerization | |
|---|---|
| $C_6$ Olefin Selectivity | % |
| 4-m-2-$C_5$= | 14.6 |
| 3-, 4-m-1-$C_5$= | 9.4 |
| 2-m-2-$C_5$= | 32.2 |
| 2-m-1-$C_5$= | 4.3 |

TABLE 1-continued

| $C_6$ Olefin Composition From Propylene Oligomerization | |
|---|---|
| $C_6$ Olefin Selectivity | % |
| 3-m-2-$C_5$= | 10.4 |
| n-$C_6$= | 0.8 |
| 2,3-dm-$C_4$= | 28.3 |

Example 6

The catalyst of EXample 4 (Ni-Zn-HZSM-5) was tested for propylene conversion at the same conditions as in Example 5. At 40 hours on stream, conversion to $C_6+$ was over 98 wt % (FIG. 1), with selectivity to dimer at 71 wt % (FIG. 2). This shows the surprising benefit of Ni addition to HZSM-5 in terms of both activity and selectivity to dimer. The propylene dimer distribution is given in Table II.

TABLE II

| $C_6$ Olefin Composition From Propylene Oligomerization | |
|---|---|
| $C_6$ Olefin Selectivity | % |
| 4-m-2-$C_5$= | 50.7 |
| 3-, 4-m-1-$C_5$= | 6.1 |
| 2-m-2-$C_5$= | 8.7 |
| 2-m-1-5= | 1.2 |
| 3-m-2-$C_5$= | 0.2 |
| n-$C_6$= | 26.8 |
| 2,3-dm-$C_4$= | 6.3 |

Example 7

For comparison, a 5% Ni on amorphous $SiO_2$-$Al_2O_3$ was prepared by pore-fill impregnation of a 40/60 $SiO_2$-$Al_2O_3$ cogel with an aqueous nickel acetate solution, drying at 300° F. overnight, then calcining in air for eight hours at 850° F. When tested for propylene conversion at the conditions of Example 5, conversion of $C_6+$ at 40 hours on stream was 54 wt %, with 40 wt % selectivity to dimer.

Example 8

The catalyst of Example 3 (Ni-HZSM-5) was tested for propylene conversion at 1000 psig and 1.0 LHSV. At 200 hours on stream, conversion to $C_6+$ at 120° F. was 73 wt % with 80 wt % of which was dimer.

Example 9

The catalyst of Example 2 (Zn-HZSM-5) was tested for propylene conversion at 0 psig, 550° F., and 2 LHSV under olefin gas phase conditions. After 90 hours on stream, conversion to $C_6+$ was 80 wt % with 25 wt % selectivity.

Example 10

The catalyst of Example 3 (Ni-HZSM-5) was tested for propylene conversion at the same conditions as in Example 9. At 70 hours on stream, conversion to $C_6+$ was 30 wt %. This shows that the addition of Ni to HZSM-5 is only beneficial when oligomerization is carried out under substantially liquid phase conditions.

Example 11

The catalyst of Example 4 (Ni-Zn-HZSM-5) was tested for propylene conversion at 0.5 LHSV and 1600 psig. A plot of catalyst temperature for 90% conversion to $C_6+$ (76 wt % to 78 wt % selectivity to dimer)

versus time on stream is shown in FIG. 3. At 430 hours on stream, the reactor pressure was reduced to 800 psig. The catalyst operated 800 hours before requiring a temperature of 180° F. for 90% conversion to $C_6+$. The selectivity to dimer was essentially unchanged. Product inspections are shown in Table III.

TABLE III $C_5+$ Product Inspections From Oligomerizing Propylene at 1600 psig and 0.5 LHSV

| | |
|---|---|
| Temperature | 120 |
| Conversion to $C_5+$, wt % | 85 |
| Gravity, API | 74.0 |
| Research Octane No., clear | 94.0 |
| Simulated TBP Distillation LV %, °F. | |
| 10/20 | 135/139 |
| 30/50 | 141/154 |
| 70/90 | 161/283 |
| Paraffins, LV % | 0 |
| Olefins, LV % | 100 |
| Naphthenes, LV % | 0 |
| Aromatics, LV % | 0 |

Example 12

The $C_6+$ product of Example 6, containing about 71 wt % propylene dimer, was processed over the Ni-Zn-HZSM catalyst of Example 4 at 800 psig, 0.5 LHSV, and 300° F. to convert greater than 60% of the feed to 350° F.+, of which about 60 wt % is propylene tetramer.

What is claimed is:

1. A process for preparing olefinic tetramer comprising:
    (a) contacting in a first stage a $C_3$ or $C_4$ olefin stream or mixture thereof, in the liquid state with an Ni-HZSM-5 catalyst at a temperature of from about 80° to 200° F. and a pressure of about 400 to 1600 psig to produce a first effluent containing at least 70% by weight dimer of said $C_3$ or $C_4$ olefin; and
    (b) contacting in a second stage the first effluent in the liquid state with a second Ni-HZSM-5 catalyst at a temperature of from about 250° to 450° F. and a pressure of 200 to 800 psig to produce a second effluent containing at least 60% tetramer of said $C_3$ or $C_4$ olefin or mixture thereof.

2. The process of claim 1 wherein the olefin in step (a) is propylene.

3. The process of claim 1 wherein the nickel-containing HZSM-5 catalyst of step (a) also contains zinc cation.

4. The process of claim 1 wherein the nickel-containing HZSM-5 catalyst of step (b) also contains zinc cation.

5. The process of claim 1 wherein said contacting in step (a) is carried out at an LHSV of from about 0.5 to 2.

6. The process of claim 1 wherein said contacting in step (b) is carried out at an LHSV of from about 0.5 to 4.

7. The process of claim 1 further comprising the step of hydrogenating at least part of said second effluent.

8. The process of claim 1 further comprising separating unreacted $C_3$ or $C_4$ olefins from said first effluent; and recycling the olefin so separated back into the feed of step (a).

9. The process of claim 1 further comprising separating unreacted $C_3$ or $C_4$ olefin dimer from said second effluent; and recycling the dimers so separated back into the feed for step (b).

10. The process of claim 1 further comprising the steps of: periodically stopping the contacting with the catalyst of step (a), step (b), or both, stripping said catalyst with a stripping gas, and resuming said contacting.

* * * * *